United States Patent
Cornelis

(10) Patent No.: US 10,888,440 B2
(45) Date of Patent: Jan. 12, 2021

(54) INTRAOSSEOUS STENT

(71) Applicant: CENTRE HOSPITALIER UNIVERSITAIRE DE BORDEAUX, Talence (FR)

(72) Inventor: Francois Cornelis, Talence (FR)

(73) Assignee: CENTRE HOSPITALIER UNIVERSITAIRE DE BORDEAUX, Talence (FR)

( * ) Notice: Subject to any disclaimer, the term of this patent is extended or adjusted under 35 U.S.C. 154(b) by 0 days.

(21) Appl. No.: 16/320,495

(22) PCT Filed: Jul. 26, 2017

(86) PCT No.: PCT/FR2017/052077
§ 371 (c)(1),
(2) Date: Jan. 25, 2019

(87) PCT Pub. No.: WO2018/020150
PCT Pub. Date: Feb. 1, 2018

(65) Prior Publication Data
US 2019/0269531 A1 Sep. 5, 2019

(30) Foreign Application Priority Data
Jul. 27, 2016 (FR) ..................................... 16 57214

(51) Int. Cl.
*A61B 17/70* (2006.01)
*A61F 2/82* (2013.01)
*A61B 17/88* (2006.01)

(52) U.S. Cl.
CPC ............ *A61F 2/82* (2013.01); *A61B 17/7097* (2013.01); *A61B 17/8858* (2013.01); *A61B 17/8855* (2013.01); *A61F 2250/0048* (2013.01)

(58) Field of Classification Search
CPC ............... A61F 2/82; A61F 2250/0048; A61B 17/7097; A61B 17/8858; A61B 17/8855
USPC .......... 623/1.11, 1.15, 1.3, 1.35, 1.44, 17.11; 606/92–94, 63, 300
See application file for complete search history.

(56) References Cited

U.S. PATENT DOCUMENTS 5,954,724 A 9/1999 Davidson
8,128,626 B2 3/2012 Justin
(Continued)

FOREIGN PATENT DOCUMENTS

EP 2 127 608 12/2008
WO WO 2007/144782 12/2007
(Continued)

OTHER PUBLICATIONS

Written Opinion in International Application No. PCT/FR2017/052077, dated Nov. 17, 2017, pp. 1-5.

*Primary Examiner* — Eduardo C Robert
*Assistant Examiner* — David C Comstock
(74) *Attorney, Agent, or Firm* — Saliwanchik, Lloyd & Eisenschenk

(57) ABSTRACT

The invention relates to a self-expanding intraosseous stent (100) intended to contain intraosseous cement, characterized in that the stent comprises a central part (101) and two lateral parts (102, 103) arranged on either side of the central part and extending along the same longitudinal axis (X), and in that the central part has a radial force lower than the radial force of the lateral parts.

13 Claims, 2 Drawing Sheets

(56) References Cited

U.S. PATENT DOCUMENTS

Figure 1:
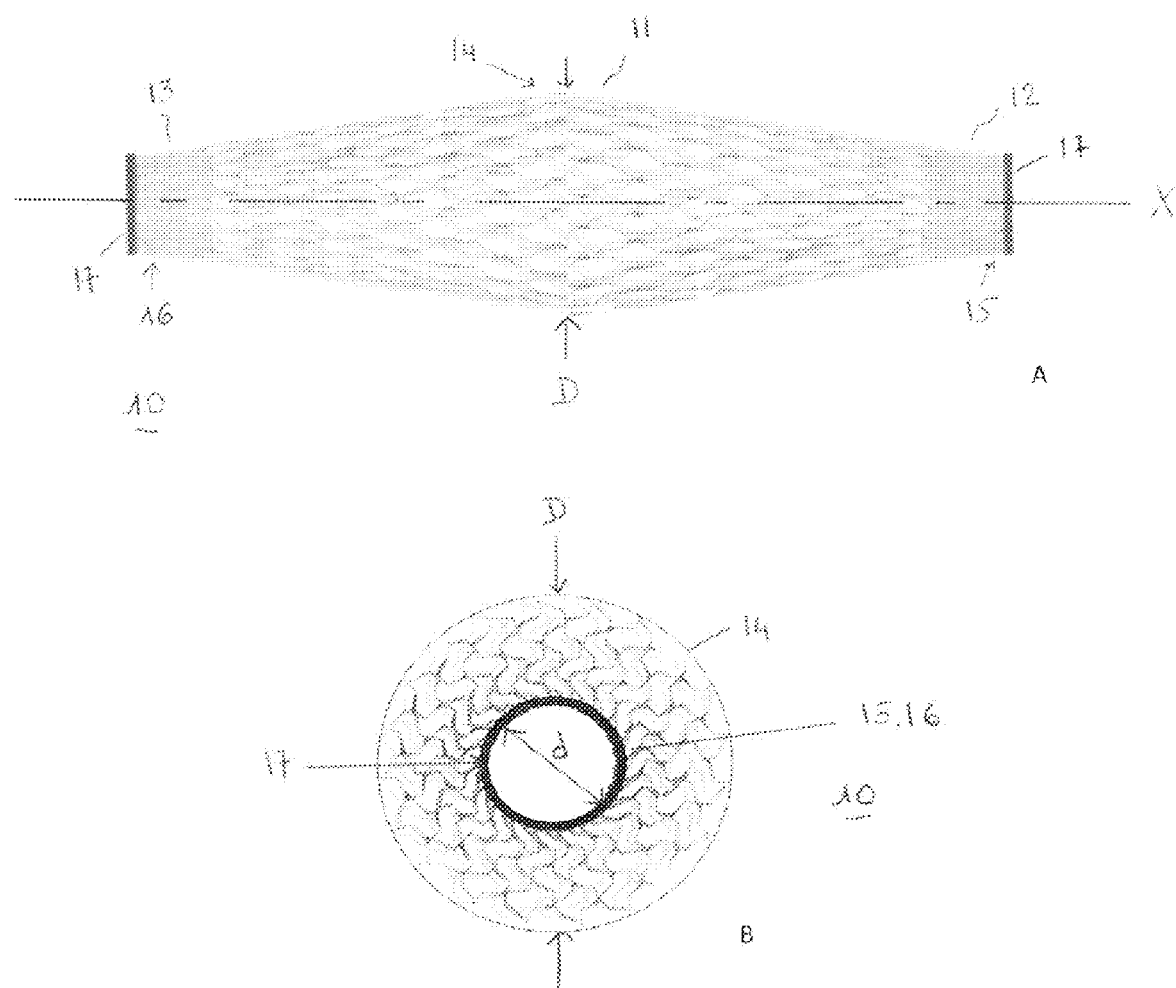

| | | | | |
|---|---|---|---|---|
| 2002/0032444 A1* | 3/2002 | Mische | ............ | A61B 17/7258 |
| | | | | 606/63 |
| 2008/0051877 A1 | 2/2008 | Hsiao et al. | | |
| 2008/0255560 A1* | 10/2008 | Myers | ................ | A61B 17/7225 |
| | | | | 606/63 |
| 2008/0269776 A1* | 10/2008 | Justin | ................ | A61B 17/7044 |
| | | | | 606/129 |
| 2015/0112418 A1 | 4/2015 | Argentine | | |
| 2017/0266006 A1 | 9/2017 | Fischer | | |

FOREIGN PATENT DOCUMENTS

| | | |
|---|---|---|
| WO | WO 2008/076357 | 6/2008 |
| WO | WO 2014/044209 | 3/2014 |
| WO | WO 2016/059026 | 4/2016 |

\* cited by examiner

INTRAOSSEOUS STENT

CROSS-REFERENCE TO RELATED APPLICATION

This application is the U.S. national stage application of International Patent Application No. PCT/FR2017/052077, filed Jul. 26, 2017.

The invention relates to a self-expanding stent intended to be introduced into a bone cavity and to contain intraosseous cement. The stent according to the invention is particularly suitable for the consolidation of a weakened bone, in particular a vertebral body or a pathological (malignant or benign) lytic bone lesion.

For several years, the percutaneous injection of cement, such as cementoplasty, has developed in order to fill lytic bone lesions (osteolytic metastases). This injection of cement, in particular polymeric cement, should enable intraosseous filling with mechanical properties substantially equivalent to those of the damaged bone. Advantageously, this bone consolidation is generally accompanied by a rapid reduction in bone pain in the patient.

Initially, the developed systems made it possible to directly inject cement into the area to be treated (under radiological control). Thus, cementoplasty is performed by percutaneous injection of cement through a needle, or trocar, introduced directly into the affected vertebral body or bone. Cementoplasty is in particular used in the treatment of osteoporotic fractures or, in some tumors, for strengthening the affected vertebrae. However, there are high risks of cement leakage to the outside of the bone body, due to the absence of stress during the injection. However, due to the vascularization of the areas to be treated, the cement can quickly end up in the venous system of the patient, with high risks of migration at epidural and/or pre-vertebral veins, which may lead to cause pulmonary embolism.

In recent years, systems to reduce vertebral fractures using vertebral stents have been implemented. The stent is most often introduced simultaneously with the balloon. The inflation of the balloon enables the deployment of the stent that maintains the opening of the vertebral body between the step of removing the balloon and the cement injection. The pressure applied remains high. This technology, known in particular as "Stentoplasty" or VBS for "Vertebral Body Stenting" further has the advantage of containing the majority of the cement in the stent volume, thereby limiting the risks of leakage.

The current systems used to perform a stentoplasty are particularly dedicated to the treatment of traumatic vertebral fractures and cannot be easily transposed to the treatment of other bone lesions, caused in particular by metastatic intraosseous cancers. Indeed, the pressure used is prohibitive, the risk of associated tumor migration being too high. In addition, the osteolytic nature of the lesions does not allow the deployment of this equipment in a healthy area.

Therefore, there is currently no stent suitable for intraosseous use at the osteolytic lesions and making it possible to contain intraosseous cement, by limiting the risks of leakage.

The objective of the invention is to at least partially solve the problem set out above, by proposing a self-expanding stent able to be deployed without pressure in a bone cavity, such as a lytic bone lesion, and to contain intraosseous cement. More particularly, the stent according to the invention is able to be deployed in two stages into the cavity. The stent is introduced in a radially compressed state into the patient's body up to the cavity where it is released. According to the invention, the hollow stent has advantageously open ends. When the stent is released, the ends of the stent, intended to be anchored into the bone bordering the bone cavity to be treated, are deployed autonomously, due to a high radial force. The central part of the stent has, for its part, a lower radial force. It is the subsequent injection of cement that will advantageously enable the more or less full radial deployment of this central part. More specifically, after the stent is placed in the cavity, surgical cement is introduced into the lumen of the stent, for example through one of the ends of said stent, and spreads into the internal volume of the stent. Thus, the intraosseous stent according to the invention has two ends, advantageously fixed to the bone once positioned in the bone cavity, and a central part extending into said cavity and intended to contain surgical cement. Advantageously, the ends of the stent are open but have a diameter which is strictly smaller than the diameter of the central part, in particular in order to limit the risks of cement leakage through said ends.

The invention therefore relates to a self-expanding intraosseous stent intended to contain intraosseous cement, characterized in that it comprises a central part and two lateral parts arranged on either side of the central part and extending along the same longitudinal axis, and in that the central part has a radial force lower than the radial force of the lateral parts.

According to the invention, the stent is a self-expanding stent, for example made of a shape-memory material, so that once placed and released in the bone cavity, the stent is deployed to recover at least partially its initial shape. The subsequent injection of cement into the stent also contributes to the expansion of the stent by the low pressure delivered during said injection.

In the context of the invention, "radial force" means resistance to an external compressive force applied to the stent.

According to the invention, the radial force of the stent enables said stent to be radially deployed into the cavity after it is placed therein, that is to say in a direction perpendicular to the largest axis of said stent. The subsequent injection of the cement contributes to the full deployment of the stent in the bone cavity, in particular to the deployment of the central part.

In a preferred embodiment, the central part of the stent has a diameter greater than the diameter of the lateral parts. For example, the ratio between the smallest diameter and the largest diameter of the stent is comprised between ⅒ and ½, preferably between ⅙ and ¼, more preferably approximately equal to ⅕.

Advantageously, the stent forms a meshed tubular structure. More specifically, the stent consists of a hollow structure with meshes and having a substantially cylindrical general shape. According to the invention, the diameter of the stent may vary in length. Similarly, the stent may have a circular, oval, polygonal or other section.

Generally, the meshing of the stent can for example be achieved by laser cutting of patterns in a solid wall, or from butt-welded modules to provide patterns. The meshing density depends on patterns and structural elements forming the meshing. The person skilled in the art knows how to adapt the meshing density, in particular by varying the shapes, dimensions, number of patterns and/or thickness of the structural elements forming the mesh.

Generally, the radial force can depend on the material used, the stiffness and/or the number and/or the shape of the meshing. It is thus possible to vary the meshing density in order to increase or decrease the radial force of the stent.

Thus, according to the invention, the lateral parts of the stent may have a meshing density greater than the meshing density of the central part. The person skilled in the art knows how to increase or on the contrary reduce the radial force of a stent by modulating all or part of these parameters.

In a first embodiment, the stent has a biconical, preferably integral, shape.

In the context of the invention, a "biconical" shape refers to a shape in which the largest diameter is substantially equidistant from the ends of the stent, of smaller diameter, the diameter gradually decreasing from the center towards the ends.

Advantageously, the meshing density of the lateral parts of the biconical stent is greater than the meshing density of the central part of said biconical stent.

In some cases, it is possible to provide for metal reinforcements, preferably made of steel, at the ends of the biconical tubular structure. Such reinforcements facilitate the anchoring of the ends in the bone bordering the bone cavity and thus allow said stent to be held in position in said cavity.

In a second embodiment, the ends of the stent are added onto the central part and secured to said central part by any means, in particular by welding or meshing entanglement.

The meshing density of the lateral parts of such a modular stent is advantageously greater than the meshing density of the central part.

In another embodiment, the stent according to the invention consists of two coaxial meshed tubes. More specifically, the meshed inner tube is longer than the meshed outer tube, so that ends of the inner tube protrude from the outer tube. Thus, the outer tube forms the central part of the stent, while the ends of the inner tube form the lateral parts of said stent.

In such an embodiment, the size of the patterns forming the meshing of the inner tube is advantageously larger than the size of the patterns forming the meshing of the outer tube. Thus, the surgical cement injected into the stent from the inner tube can escape into the volume of the outer tube at which it is retained. The meshing density of the inner tube is then generally lower than the meshing density of the outer tube.

The thickness of the structural elements forming the meshing of the inner tube may be significant, so as not to penalize the radial force of the inner tube. In addition, in order to increase the radial force of the inner tube, it is possible to use an inner tube made of steel and/or chromium-cobalt alloy. The outer tube can for example be made, for its part, of nickel-titanium alloy (Nitinol).

Advantageously, the inner tube is fixed in translation into the outer tube, so as to avoid any movement of one tube with respect to the other during manipulation, and in particular during introduction of the stent into the lytic cavity and/or deployment before cement injection. The tubes can be fixed by any known means, and in particular by entanglement of meshes, local welds, etc.

Generally, the intraosseous stent according to the invention may be at least partially covered with a leak-proof outer membrane, helping to prevent or limit cement leakage. Advantageously, such an outer membrane is made of, at least partially sealed, stretchable or elastic material. Advantageously, the outer membrane conforms to an outer contour of the stent. Preferably, at least the central part of the stent is covered with such a leak-proof membrane. In a particular exemplary embodiment, the membrane is made of polymer, and in particular of polytetrafluoroethylene (PTFE).

The stent can have different dimensions (including length and diameter) which are variable based on the nature and extent of the bone cavity to be treated. The stent generally does not fill the entire cavity, but must at least allow forming a pillar in said cavity to distribute stresses between the regions of the intraosseous body around the cavity. For example, the tubular structure can have a length, or a larger dimension, comprised between 40 and 80 mm, for a larger diameter comprised between 10 and 20 mm. The person skilled in the art knows how to adapt the length and diameter of the stent based on the dimensions, nature and location of the cavity.

The invention also relates to an intraosseous surgical cement injection kit comprising, in addition to an intraosseous stent according to the invention, a system for the introduction of a stent into a bone lesion and possibly a surgical cement injection means and/or surgical cement. For example, the introduction system comprises a cannula on which the stent is mounted, and capable of introducing said stent up to the lytic bone lesion to be treated. The cement injection means may, for its part, consist of a syringe, possibly equipped with a needle.

According to the invention, any surgical cement suitable for intraosseous use can be used. As a non-limiting example, PMMA-type cements (Polymethacrylate), commonly used in vertebroplasty, can be mentioned.

Figure 2:
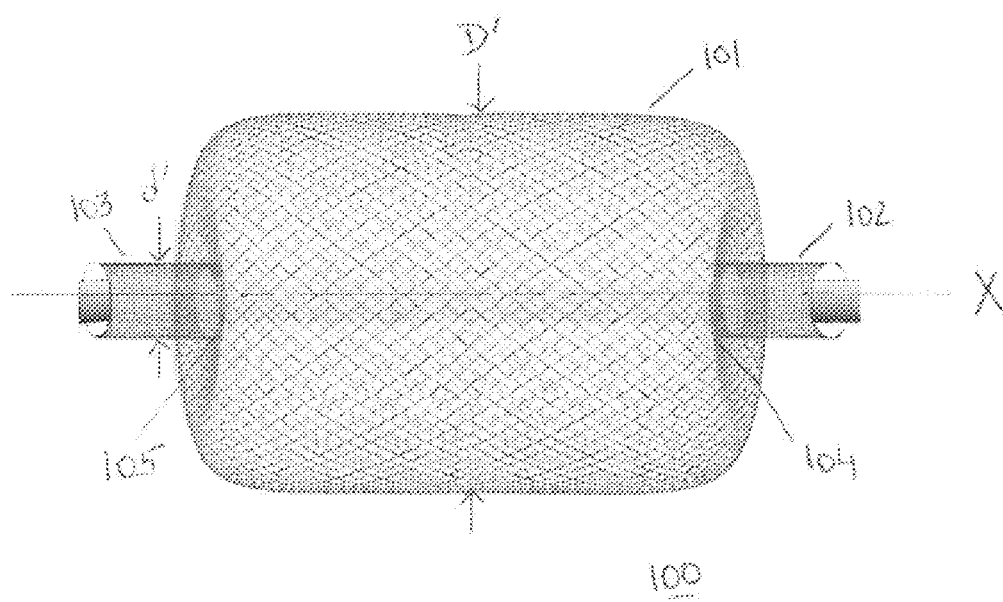
Figure 3:
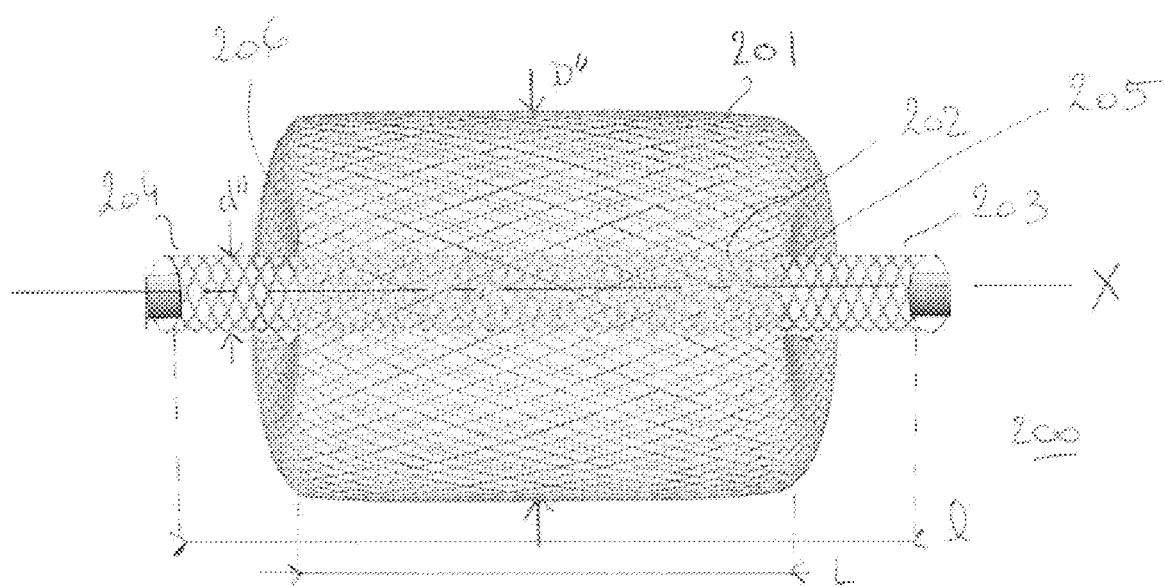

The invention will be better understood upon reading the following description and upon examining the accompanying figures. These are presented for illustrative purposes and are not limited to the invention. The figures represent:

FIG. 1: Schematic representation seen from the side (A) and the front (B) of an intraosseous stent according to a first embodiment of the invention;

FIG. 2: Schematic representation seen from the side of an intraosseous stent according to a second embodiment of the invention;

FIG. 3: Schematic representation seen from the side of an intraosseous stent according to a third embodiment of the invention.

FIG. 1 represents an intraosseous stent according to a first embodiment of the invention. The intraosseous stent 10 with a generally biconical shape, is intended to be housed in a bone cavity. The stent 10 comprises a central part 11 and two lateral parts 12, 13 arranged coaxially on either side of the central part 11. The central part 11 has an area 14 of larger diameter D substantially equidistant from the ends 15, 16 of smaller diameter d of the lateral parts 12, 13. The diameter of the stent 10 gradually decreases from the area 14 of larger diameter D up to the ends 15, 16 of smaller diameter d.

The ends 15, 16 of the stent 10 are each reinforced by a metal ring 17, such as a steel ring. These metal rings facilitate the anchoring of the ends 15, 16 of the lateral parts in the bone surrounding the bone cavity in which said stent is intended to expand.

The meshing density of the central part 11 is lower than the meshing density of the lateral parts 12, 13. For example, the dimensions of the patterns forming the meshing are larger at the central part 11 than at the lateral parts 12, 13. More specifically, in the example shown in FIG. 1, the dimensions of the patterns decrease from the area 14 of larger diameter up to the ends 15, 16. Alternatively or additionally, the structural elements providing the patterns and therefore the mesh, are thicker at the lateral parts 12, 13 than at the central part 11. This meshing density which is more significant at the lateral parts 12, 13 contributes to increasing the radial force of said lateral parts 12, 13 compared to the central part 11.

Such a stent 10 can be made for example of Nitinol or chromium-cobalt alloy.

According to the invention, it is possible to cover at least the central part 11, having large meshes, with a leak-proof film (not shown) to reduce the risks of cement leakage between said meshes.

FIG. 2 represents an intraosseous stent according to a second embodiment of the invention. The 100 stent comprises a central part 101, at the ends of which lateral parts 102, 103 are added and fixed. The lateral parts 102, 103 extend coaxially on either side of the central part 101.

In this embodiment, the central part 101 has a diameter D' that is substantially constant over the entire length (or larger dimension). Similarly, the lateral parts 102, 103 have a diameter d' that is substantially constant over the entire length, the diameter d' of the lateral parts 102, 103 being strictly smaller than the diameter D' of the central part 101. In the example shown in FIG. 2, the ratio of d'/D' is approximately equal to ⅕.

The lateral parts 102, 103 are fixed to the ends 104, 105 of the central part 101, by any way. As shown in FIG. 2, the ends 104, 105 of the central part 101 are tightened around the lateral parts 102, 103 so as to avoid any risk of cement leakage at the junction between said lateral parts 102, 103 and the central part 101 of the stent 100.

The meshing density of the central part 101 is lower than the meshing density of the lateral parts 102, 103. For example, the dimensions of the patterns forming the meshing are larger at the central part 101 than at the lateral parts 102, 103. Alternatively or additionally, the number of patterns forming the mesh is smaller at the central part 101 than at the lateral parts 102, 103. This meshing density which is more significant at the lateral parts 102, 103 contributes to increasing the radial force of said lateral parts 102, 103 compared to the central part 101.

Such a stent 100 can be made of different materials so as to vary the radial forces. For example, the central part 101 can be made of fine Nitinol fibers and the lateral parts 102, 103 can be made of steel, chromium-cobalt alloy or with thick Nitinol fibers.

When the stent 100 is placed into the bone cavity to be treated, the lateral parts 102, 103 are deployed and anchored into the bone bordering said cavity. The deployment of the central part 101, whose radial force is smaller, is achieved during surgical cement injection into the internal volume of said central part 101. Again, it may be interesting to cover at least the central part 101, having large meshes, with a leak-proof film (not shown) to reduce the risks of cement leakage between said meshes.

FIG. 3 represents an intraosseous stent according to a third embodiment of the invention. The stent 200 comprises an outer tube 201 and an inner tube 202 extending coaxially in the internal volume of the outer tube 201.

A length L of the outer tube 201 is strictly smaller than a length l of the inner tube 202. Thus, the ends 203, 204 of the inner tube 202 extend on either side of the outer tube 201. In this embodiment, the outer tube 201 forms the central part of the stent 200, while the ends 203, 204 of the inner tube 202 form the lateral parts of said stent 200.

In this embodiment, the outer tube 201 has a diameter D" that is substantially constant over the entire length L. Similarly, the inner tube 202 has a diameter d" that is substantially constant over the entire length l, the diameter d" being strictly smaller than the diameter D". In the example shown in FIG. 3, the ratio d"/D" is approximately equal to ⅕.

Advantageously, the ends 203, 204 of the inner tube 201 are secured to the ends 205, 206 of the outer tube 201, by any means, in order to prevent any movement of the inner tube 202 with respect to the outer tube 201.

As shown in FIG. 3, the ends 205, 206 of the outer tube 201 are tightened around the ends 203, 204 of the inner tube 202. Such a tightening allows in particular avoiding the risks of cement leakage at the junction between said lateral parts and the central part of the stent 200.

In this embodiment, the meshing density of the inner tube 202 is lower than the meshing density of the outer tube 201, in order to allow the surgical cement, which will be introduced into the stent through the inner tube 202, to escape from said inner tube 202 and to extend into the internal volume of the outer tube 201. For example, the meshing of the inner tube 202 has patterns of large dimensions. In order to impart a high radial force to the inner tube 202, said inner tube 202 is advantageously made of steel or chromium-cobalt alloy with a large meshing. The outer tube 201, for its part, can be made of fine Nitinol fibers.

When the stent 200 is placed into the bone cavity to be treated, the inner tube 202 is radially deployed and the ends 203, 204 are anchored into the bone bordering said cavity. The deployment of the outer tube 201 is achieved during the surgical cement injection, which flows from the inner tube 202 in the internal volume of the outer tube 201.

Advantageously, the outer tube 201 and the ends 203, 204 of the inner tube 202 are covered with a leak-proof film (not shown) to reduce the risks of cement leakage between the meshes of the tubes.

The invention claimed is:

1. A self-expanding intraosseous stent intended to contain intraosseous cement, wherein the stent comprises a central part and two lateral parts arranged on either side of the central part and extending along the same longitudinal axis, and wherein the central part has a radial force lower than a radial force of the lateral parts, the stent comprising a coaxial meshed outer tube and meshed inner tube, the inner tube having a length greater than the length of the outer tube, so that ends of the inner tube protrude from the outer tube forming the central part of said stent, said ends of the inner tube forming the lateral parts of said stent, and wherein a meshing, density of the inner tube is lower than a meshing density of the outer tube.

2. The intraosseous stent according to claim 1, wherein the central part of the stent has a diameter greater than the diameter of the lateral parts of said stent.

3. The intraosseous stent according to claim 1, wherein said stent has a biconical shape.

4. The intraosseous stent according to claim 3, wherein the ends of the biconical stent are reinforced by a metal ring.

5. The intraosseous stent according to claim 1, wherein the lateral parts of the stent are secured on the central part, in particular by welding or meshing entanglement.

6. The intraosseous stent according to claim 1, wherein the inner tube is made of steel, chromium-cobalt alloy, or mixture thereof.

7. The intraosseous stent according to claim 1, wherein the outer tube is made of nickel-titanium alloy (Nitinol).

8. The stent according to claim 1, wherein the inner tube is fixed in translation into the outer tube.

9. The stent according to claim 1, wherein at least the central part of the stent is covered with a leak-proof membrane.

10. The stent according to claim 9, wherein the leak-proof membrane is made of polymer.

11. The stent according to claim 1, wherein a length of the stent is comprised between 40 and 80 mm, and the diameter of the central part of said stent is comprised between 10 and 20 mm.

12. An intraosseous surgical cement injection kit comprising a system for the introduction of a stent into a bone lesion and an intraosseous stent according to claim 1 mounted in said introduction system.

13. The intraosseous surgical cement injection kit according to claim 12, further comprising surgical cement injection means and surgical cement.

* * * * *